United States Patent
Tomooka et al.

(10) Patent No.: US 6,928,686 B2
(45) Date of Patent: Aug. 16, 2005

(54) WASHING APPARATUS FOR ENDOSCOPE

(75) Inventors: Masashi Tomooka, Tokyo (JP); Masao Suzuki, Tokyo (JP); Yoshinobu Oyama, Tokyo (JP); Taketo Suzuki, Tokyo (JP)

(73) Assignee: Koken Ltd., Tokyo (JP)

( * ) Notice: Subject to any disclaimer, the term of this patent is extended or adjusted under 35 U.S.C. 154(b) by 111 days.

(21) Appl. No.: 10/095,965

(22) Filed: Mar. 13, 2002

(65) Prior Publication Data

US 2003/0000035 A1 Jan. 2, 2003

(30) Foreign Application Priority Data

Jun. 29, 2001 (JP) ........................................ 2001-200117

(51) Int. Cl.[7] .............................. F16L 45/00; B08B 1/00
(52) U.S. Cl. ................ 15/104.2; 15/104.16; 15/104.05; 15/104.09; 134/169 C
(58) Field of Search .................... 15/104.2, 104.095, 15/104.05, 104.09, 104.096, 104.15, 104.12, 104.16, 56, 61, 64; 422/292, 300; 134/166 R, 169 C, 166 C

(56) References Cited

U.S. PATENT DOCUMENTS

| | | | | |
|---|---|---|---|---|
| 4,306,914 A | * | 12/1981 | Long ............................. | 134/1 |
| 4,546,519 A | * | 10/1985 | Pembroke ..................... | 15/395 |
| 5,251,356 A | | 10/1993 | Oaki et al. | |
| 5,619,767 A | * | 4/1997 | Larson .......................... | 15/74 |
| 5,636,403 A | * | 6/1997 | Grimsley et al. ...... | 15/104.095 |
| 6,047,431 A | | 4/2000 | Canonica | |
| 6,699,331 B1 | * | 3/2004 | Kritzler ......................... | 134/8 |

FOREIGN PATENT DOCUMENTS

JP                 8-275918            * 10/1996

OTHER PUBLICATIONS

Patent Abstracts of Japan, vol. 1997, No. 02, Feb. 28, 1997.
Patent Abstracts of Japan, vol. 018, No. 248 (C–1198), May 12, 1994.
Japanese Patent Application No. 1995–194533A.
Japanese Patent Application No. 1996–275917A.

* cited by examiner

*Primary Examiner*—Robert J. Warden, Sr.
*Assistant Examiner*—Laura C Cole
(74) *Attorney, Agent, or Firm*—Lowe Hauptman & Berner, LLP

(57) ABSTRACT

A washing apparatus for an endoscope includes a wire brush, a region for housing the wire brush and a driver adapted to advance and retract the wire brush. The wire brush is received in a pipe section of the wire housing region so that the wire brush may be selectively advanced out or retracted in this pipe section which is, in turn, provided along its front end portion and a rear end portion with position sensors to detect a position of a wire component of the wire brush.

19 Claims, 6 Drawing Sheets

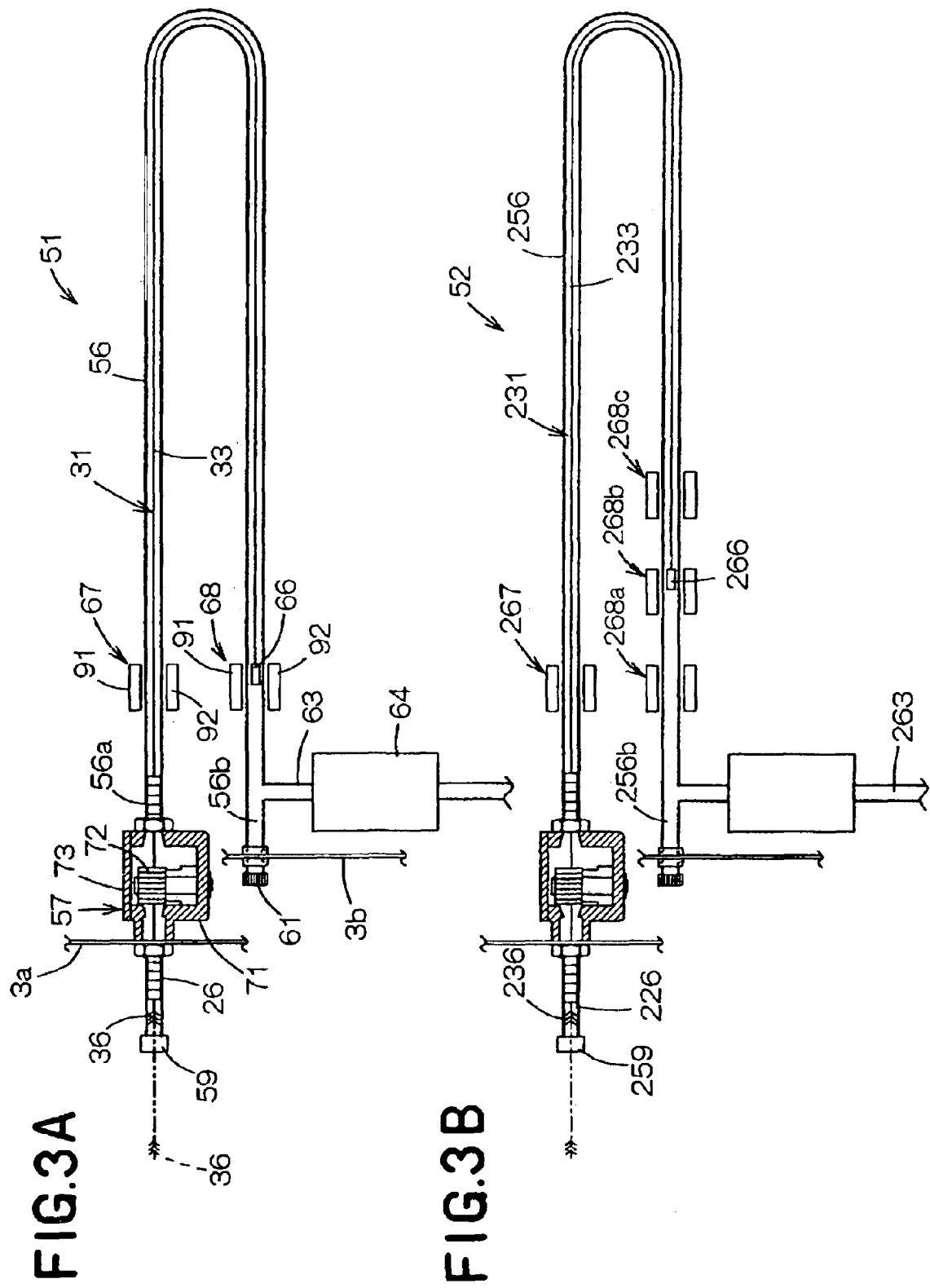

WASHING APPARATUS FOR ENDOSCOPE

BACKGROUND OF THE INVENTION

This invention relates to a washing apparatus for an endoscope using a wire brush.

Japanese Patent Application Publication Nos. 1995-194533A and 1996-275917A disclose an apparatus to wash an interior of an endoscope's conduit by automatically inserting a wire brush into the conduit of the endoscope immersed in an endoscope washing tank. The wire component is relatively long and normally taken-up on a reel, and the length thereof corresponding to the length of the conduit is pulled out from the reel prior to use.

With such a washing apparatus of well known art, the length of the wire component to be pulled out is sometimes controlled by times of revolution of the reel. However, if the wire component is not properly taken-up, for example, partially doubled on the reel, the length of the wire component pulled out is not properly related to the times of revolution of the reel. In this case, the length of the wire component to be pulled out can not be accurately controlled. In addition, one end of the wire component is fixed to the reel, and if the wire component is needed to be exchanged, the fixed end of the wire component has to be released from the reel after a troublesome operation to take the reel out from its housing.

SUMMARY OF THE INVENTION

It is an object of this invention to improve a washing apparatus for an endoscope using a wire brush so that the length of the wire brush to be advanced out for insertion thereof into the conduit of the endoscope can be accurately controlled and the wire brush can be easily exchanged.

According to this invention, there is provided a washing apparatus for an endoscope comprising a wire brush equipped with a wire component having front and rear end portions and a brush component provided along the front end portion, a region for housing the wire brush therein and a drive means adapted to advance/retract the wire brush from the housing toward a conduit of the endoscope and vice versa.

The washing apparatus for washing an endoscope further comprises a region for housing the wire brush including a pipe section adapted to receive a substantially full length of the wire brush inserted into and withdrawn from the region, the region for housing the wire brush having its front end portion being opened so as to be connected to the conduit, a drive means being provided in the vicinity of the front end portion and functioning to advance/retract the wire brush toward and from the conduit respectively, the region for housing the wire brush having its rear end portion adapted to be selectively opened and closed so that the wire brush can be inserted/withdrawn into and from the pipe section when the rear end portion is opened, a water supply means being provided in the vicinity of the rear end portion to supply the pipe section with water and, the pipe section being provided at its front and rear end portions respectively with at least one sensor to detect a position of the wire component.

This invention includes preferred embodiments as follow:

The washing apparatus for the endoscope is used in combination with a washing tank so that the region for housing the wire brush has its rear end portion lying within the washing tank and adapted to be opened and closed within the washing tank; the washing tank is adapted to receive at least a pair of the washing apparatus; the pipe section is provided along the rear end portion with three of the position sensors arranged in a longitudinal direction of the pipe section; the drive means can be operated or stopped with a signal coming from any of the position sensors; the pipe section is light transmissive; the position sensors are equipped with light emitters; and the water supply means is able to supply at least one of alkaline water, acidic water and tap water.

BRIEF DESCRIPTION OF THE DRAWINGS

FIGS. 3A and 3B are sectional views showing the washing apparatus for the endoscope according to two different embodiments (a) and (b);

DETAILED DESCRIPTION OF THE PREFERRED EMBODIMENTS

Details of a washing apparatus for an endoscope will be more fully understood from descriptions given hereunder with reference to the accompanying drawings.

Figure 1:
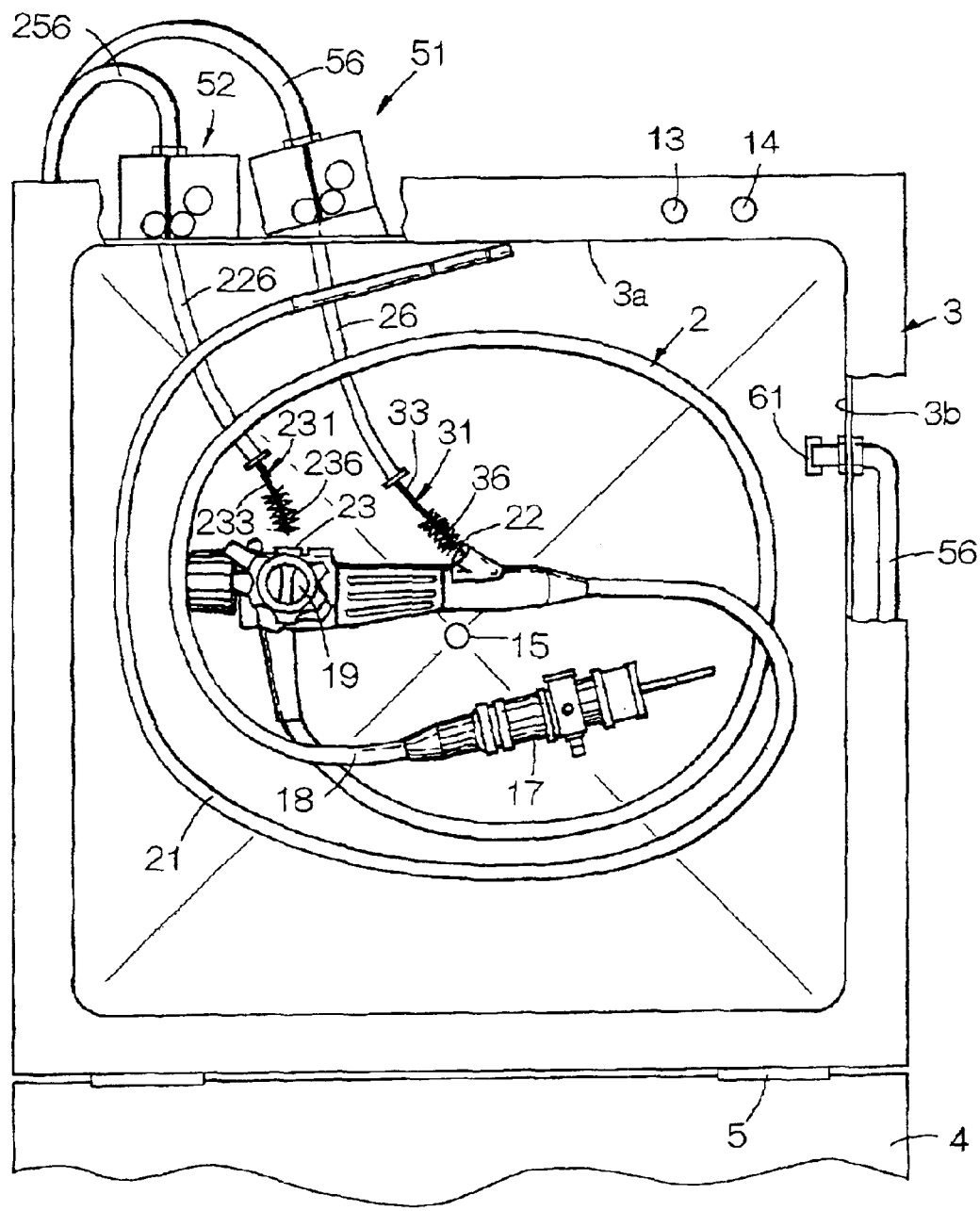
FIG. 1 is a fragmentary top view showing a washing tank in combination with a washing apparatus for an endoscope.

FIG. 1 is a top view showing a washing tank 3 used in combination with a washing apparatus for an endoscope 2, in which a cover 4 connected by means of hinges 5 to the tank 3 is illustrated to be in its opened position. The endoscope 2 is put in the washing reservoir 3 ready for washing using water supplied from outlet ports 13, 14. The washing water may be alkaline water, acidic water or tap water. Conditions for supplying the washing water can be set by a control panel (not shown). The washing water is discharged from the tank through a drain port 15. The endoscope 2 is one of common types and comprises a connector 17, a universal cord section 18, a manipulator 19 and an insert section 21. The manipulator 19 is provided with a forceps receiving port 22 and a suction button receiving port 23.

A pair of flexible connector tubes 26, 226 extend from a sidewall 3a of this washing tank 3 and a pair of wire brushes 31, 231 extend from these connector tube 26, 226 respectively. The wire brushes 31, 231 respectively comprise wire components 33, 233 and brush components 36, 236 and are adapted to be pulled out from and to be retracted into front ends of the respective connector tubes 26, 226. The connector tubes 26, 226 can be detachably connected respectively to the forceps receiving port 22 and the suction button receiving port 23 of the endoscope 2. The wire components 33, 233 of the respective wire brushes 31, 231 may be repeatedly moved back and forth through a conduit of the endoscope 2 to brushing-wash inside of the conduit.

Alkaline water to be supplied as the washing water preferably has pH of 11.0 or higher and oxidation-reduction potential (ORP) of −800 mV or higher. Such alkaline water is suitable to dissolve blood or other proteins clinging to the endoscope 2 which is already used. Acidic water supplied as washing water preferably has pH lower than 2.7 and oxidation-reduction potential of +1100 mV or higher. Such acidic water is suitable as germicide against bacteria or the like. Tap water is used to rinse the endoscope 2 before and after sterilization thereof.

Figure 2:
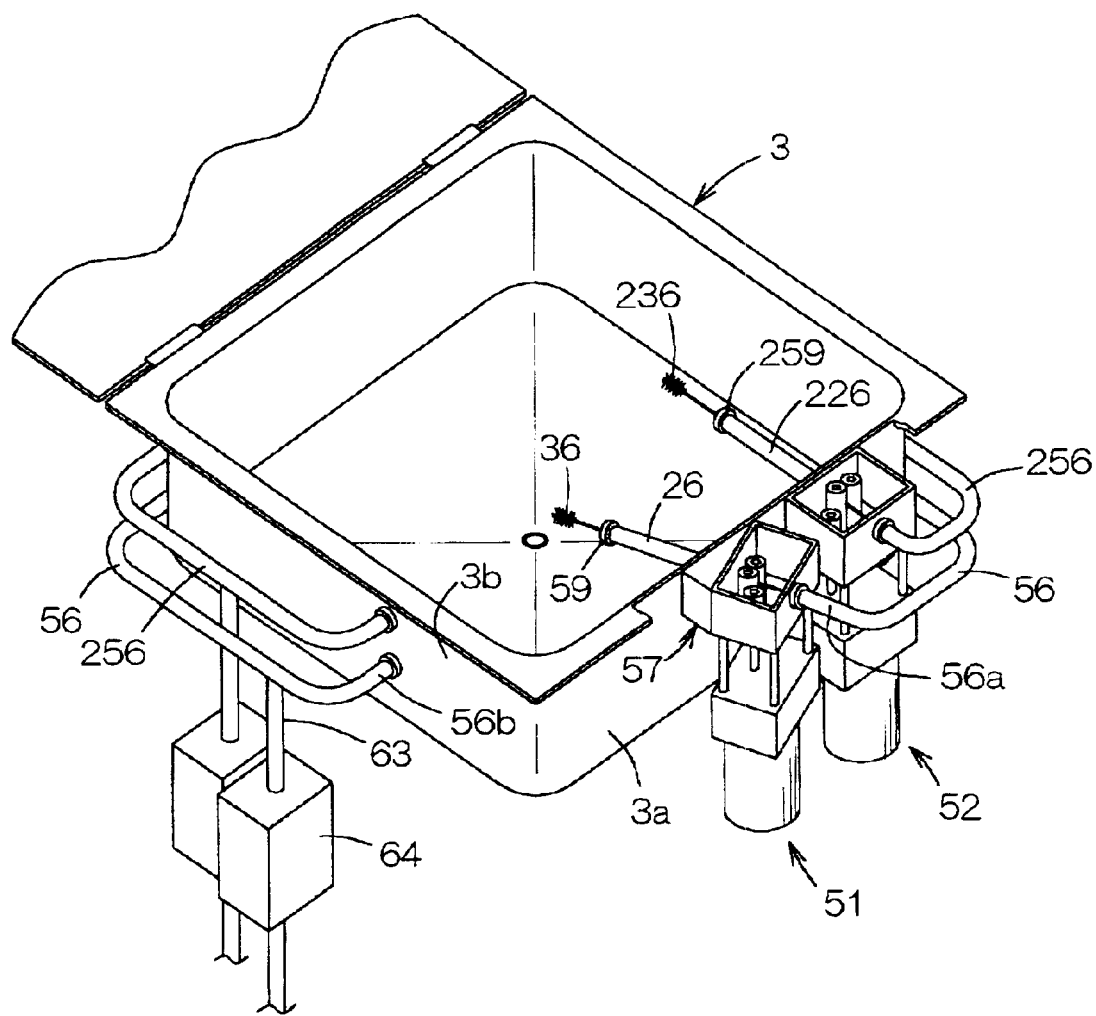
FIG. 2 is a perspective view of the washing tank shown in FIG. 1.
Figure 3C:
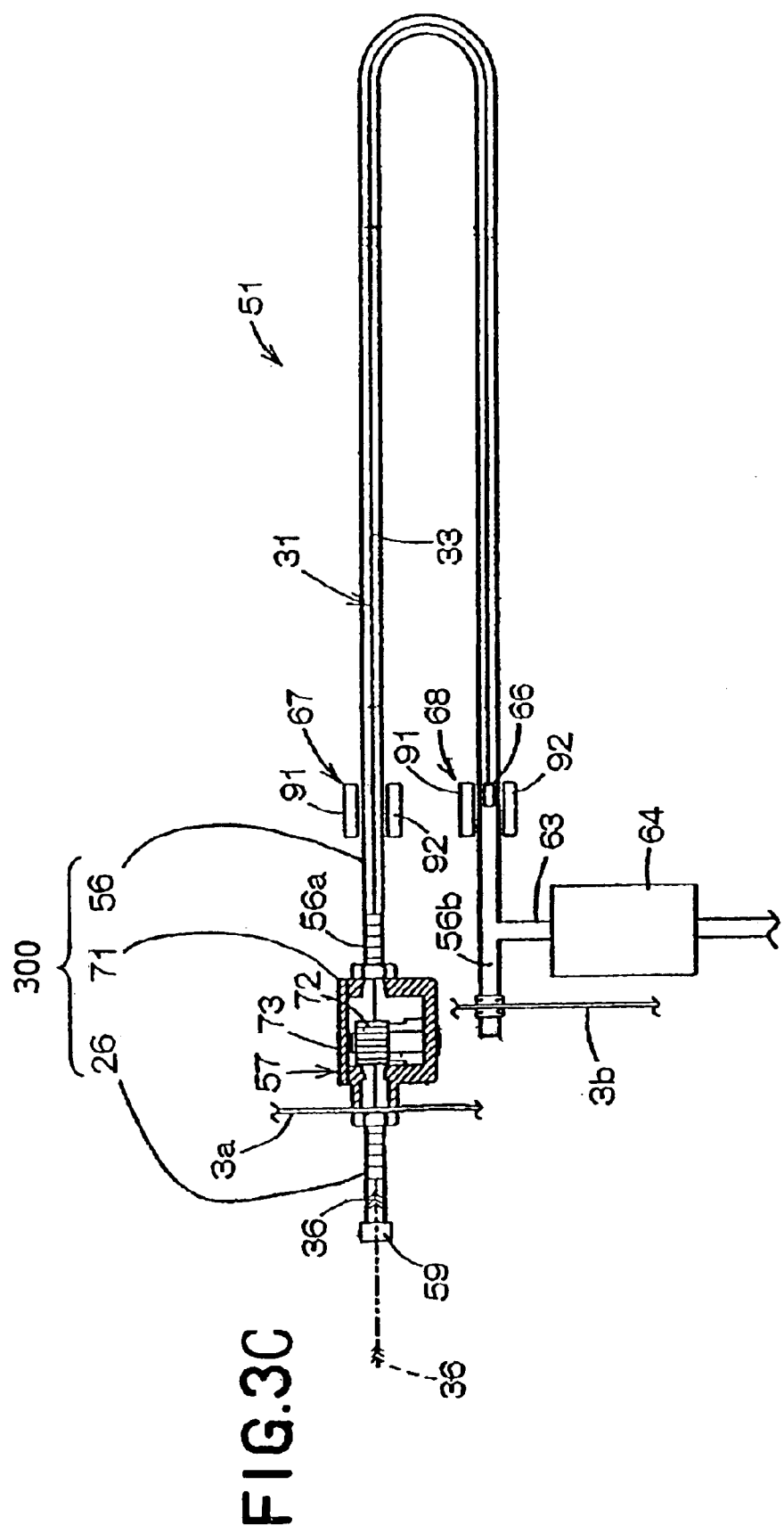
FIG. 3C is a sectional view similar to FIG. 3A showing the rear end portion of the pipe section of the apparatus in accordance with the first embodiment extending into the washing tank and being left opened.

FIG. 2 is a perspective view of a major part of the washing tank 3. On the outer side of the washing tank 3, there are mounted a first washing device 51 and a second washing device 52 constituting the washing apparatus for the endoscope 2 according to this invention. Since the first washing device 51 and the second washing device 52 are substantially identical in their configurations, the first washing device 51 will be described first. The first washing device 51 includes a housing 300 (See FIG. 3C) that includes a pipe section 56 extending so as to surround the washing tank 3 and the pipe section 56 is provided on its front end portion 56a with a drive means 57 fixed to the outer side of the side wall 3a of the washing tank 3. From the drive means 57, the connector tube 26 extends into the washing tank 3. The connector tube 26 is provided at its front end portion with an attachment 59 to the forceps receiving portion 22 (See FIG. 1) of the endoscope 2. A rear end portion 56b of the pipe section 56 extends into the washing tank 3 and is provided with a detachable stopper 61 (See FIG. 3(a)). The rear end portion 56b is water-tightly fixed to the side wall 3b of the washing tank 3. In the vicinity of the rear end portion 56, a water supply pipe 63 is connected with an electromagnetic valve 64. Inside the washing tank 3, a front end portion of the wire brush 31 is exposed from the attachment 59.

(a) and (b) in FIG. 3 are sectional views showing the first washing device 51 and the second washing device 52 respectively. In the first washing device 51, the wire component 33 of the wire brush 31 longitudinally extends within the pipe section 56 and a substantially full length of the wire brush 31 extends between the connector tube 26 and the stopper 61 of the device 51. The wire component 33 is provided along its front end portion with the brush component 36 and along its rear end portion with a light shielding plate 66. The pipe section 56 is provided in the vicinity of its front end portion 56a slightly behind the drive means 57 with a front sensor 67 and in the vicinity of its rear end portion 56b slightly in front of the stopper 61 with a rear sensor 68. These sensors 67, 68 are identical to each other and respectively comprise light emitters 91 and light receivers 92 opposed to each other in a diametrical direction of the light transmitting pipe section 56 with the latter therebetween. The wire brush 31 is illustrated to be in its retracted state and the light shielding plate 66 is facing to the rear sensor 68. Consequently, the light shielding plate 66 shields the light from the light emitter 91 and the rear sensor 68 detects that the wire brush 31 is in its retracted state and transmits a detection signal to the drive means 57 via an appropriate control circuit. When the wire brush 31 is advanced out and the light shielding plate 66 correspondingly moves to the position of the front sensor 67, the light shielding plate 66 shields the light from the light emitter 91 and the front sensor 67 detects that the wire brush 31 is in its advanced out position. The front sensor 67 transmits a detection signal to the drive means 57. The drive means 57 comprise a housing 71 and a roller 72 instelled in this housing 71 which is, in turn, in a water-tight state except for the pipe section 56 and the connector tube 26. The water supply pipe 63 connected to the pipe section 56 in the vicinity of its rear end portion 56b includes the electromagnetic valve 64 which may be controlled for selective supply of alkaline water, acidic water or tap Water to the pipe section 56 as washing water.

Figure 4:
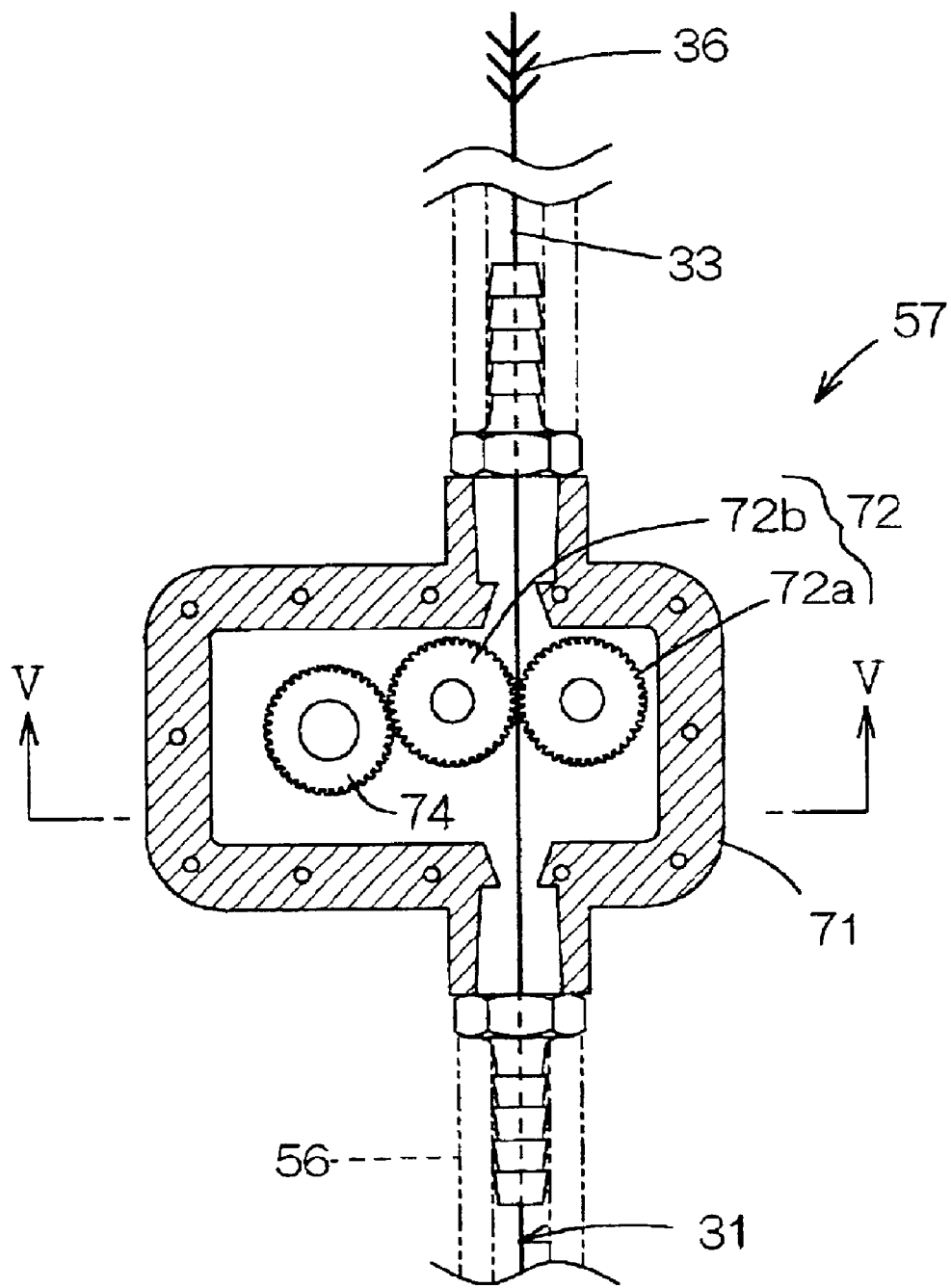
FIG. 4 is a top view of a drive means.
Figure 5:
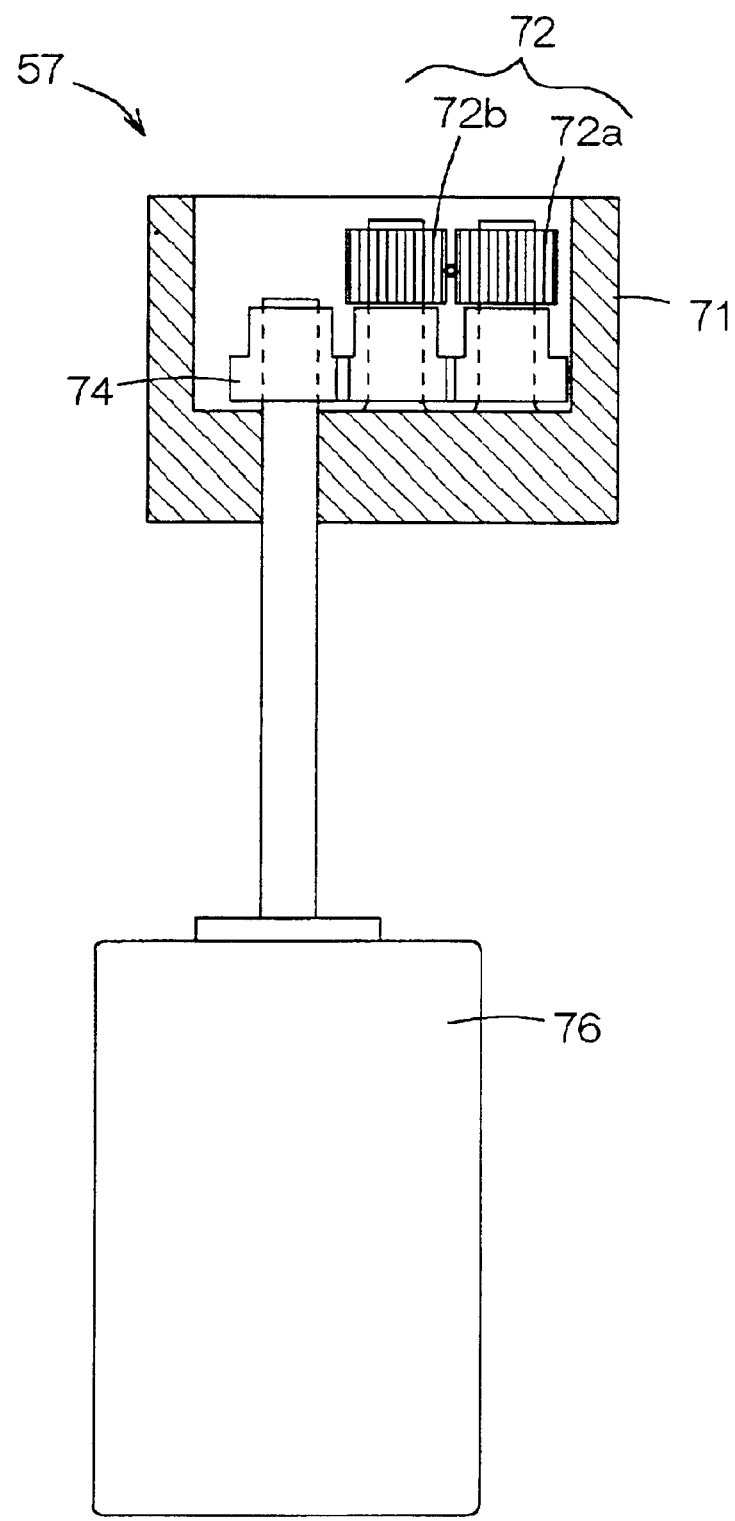
FIG. 5 is a sectional view taken along a line V—V in FIG. 4.

FIGS. 4 and 5 are a top view of the drive means 57 and a fragmentary sectional view taken along a line V—V in FIG. 4. In FIG. 4, the housing 71 enclosing the drive means 57 is illustrated with its cover 73 (See FIG. 3(a)) removed so that the inside of the housing 71 can be seen. The roller 72 of the drive means 57 specifically comprises a pair of rollers 72a, 72b arranged side by side, which roller 72a, 72b are rotated to squeeze out the wire component 33 of the wire brush 31 therebetween at an appropriate pressure. Thereby the wire brush 31 can be selectively advanced out or retracted and, in addition, the wire brush 31 can be guided by these rollers 72a, 72b selectively for insertion into or withdrawal from the pipe section 56. The roller 72 is rotated by a driving gear 74 and an electric motor 76 shown in FIG. 5 operatively associated with the driving gear 74. The electric motor 76 can be rotated clockwise or counterclockwise or stopped with the signals supplied from the front sensor 67 and the rear sensor 68.

With the first washing device 51 of such an arrangement, the attachment 59 of the connector tube 26 is fixed to the forceps receiving port 22 of the endoscope 2 shown in FIG. 1. If the wire brush 31 is exposed from the connector tube 26 at this time point, the wire brush 31 must be previously inserted into the port 22. Then, the attachment 259 of the connector tube 226 of the second washing device 52 is fixed to the suction button receiving port 23 of the endoscope 2. Upon starting of washing operation using the control panel of the washing tank 3, the electromagnetic valve 64 of the water supply pipe 63 is opened so that alkaline water, acidic water or tap water is selectively supplied depending on the particular condition set by the panel. At the start of washing operation, the wire brush 31 is in its retracted state with the light shielding plate 66 lying at the position facing to the rear sensor 68. Upon starting, the drive means 57 causes the rollers 72a, 72b to advance the wire brush 31 progressively so that the wire brush 31 may be repeatedly advance and retracted within a forceps channel (not shown) of the endoscope 2. As soon as the light shielding plate 66 of the wire brush 31 reaches the front sensor 67, the wire brush 31 is stopped with the signal from the light shielded front sensor 67. Thereafter, the rollers 72a, 72b are rotated to retract the wire brush 31 so that the wire brush 31 may be repeatedly advanced or retracted, or simply retract the wire brush 31 until the light shielding plate 66 reaches the rear sensor 68. Normally, such an operation of washing is performed using alkaline water, acidic water and tap water respectively before the conduit (i.e., channel) of the forceps of the endoscope 2 is completely washed. However, a time taken for washing or the number of repetition of washing largely depends on each of the washing waters. In the course of washing the endoscope 2 in this manner, the wire brush 31 itself is also washed. The wire brush 31 linearly extends within the pipe section 56 instead of being taken up on a reel as the prior art has been the case, so the wire component 33 as well as the brush component 36 are completely washed. The wire brush 31 preferably has a length such that the brush component 36 lies in front of the forceps receiving port 22 when the light shielding plate 66 faces to the rear sensor 68 and reaches the front end portion of the conduit for the forceps when the light shielding plate 66 faces to the front sensor 67. The pipe section 56 also preferably has a length corresponding thereto.

For insertion or withdrawal of the wire brush 31 with respect to the pipe section 56, the stopper 61 may be released within the washing tank 3 (See FIG. 3C) and the rear end portion 56b of the pipe section 56 may be opened. Since the rear end portion 56b lies within the washing tank 3, there is no possibility that washing water supplied to the pipe section 56 leaks out to the room even if the rear end portion 56b is left open or the stopper 61 is not properly sealing the rear end portion 56b. It is to be noted that the first washing device 51 can be used in a condition that the rear end portion 56b of the pipe section 56 is disconnected from the washing tank 3 and the rear end portion 56b is sealed with the stopper 61. It is also possible to use the device 51 inclusive of the drive means 57 and the connector tube 26 disconnected from and therefore independent of the washing tank 3.

The second washing device 52 shown in FIG. 3(b) is similar to the first washing device 51 shown in FIG. 3(a) except for an arrangement of the rear sensor. Accordingly, components or members similar to those in the first washing device 51 are designated by the similar reference numerals respectively with the numeral 200 added. The second washing device 52 is provided adjacent a rear end portion 256b with a first rear sensor 268a, a second rear sensor 268b and a third rear sensor 268c successively arranged in the longitudinal direction of a pipe section 256. These first-third rear sensors 268a–268c are of the same structure as a front sensor 267. This second washing device 52 is suitable for washing of the suction conduit and the universal cord section conduit (both not shown) of the endoscope 2. An attachment 259 of a connector tube 226 is fixed to the suction button receiving port 23. Upon starting of the second washing device 52 using the control panel of the washing tank 3, a wire brush 231 reaches the third rear sensor 268c as a light shielding plate 266 is advanced from a position facing to the second rear sensor 268b. During this process, a brush component 236 moves back and forth in the suction conduit of the endoscope 2 to wash this. Then, the wire brush 231 is retracted until the light shielding plate 266 moves from a position facing to the third rear sensor 268c to the first rear sensor 268a and the brush component 236 is drawn out from the suction conduit. Now the wire brush 231 repeatedly moves back and forth bit by bit until the light shielding plate 266 reaches a position facing to the front sensor 267 and, during this back and forth movement, the brush component 236 washes the universal cord section conduit. After the full length of this conduit has been washed, the wire brush 231 moves back until the light shielding plate 266 reaches the position facing to the second rear sensor 268b. During such movements of the wire brush 231, the pipe section 256 is supplied from a water supply pipe 263 with any one of alkaline water, acidic water and tap water. It should be understood that a sequence in which the first-third rear sensors 268a–268c are selected may be appropriately changed. For example, the light shielding plate 266 may be moved from the first or the third rear sensor 268a, 268c instead of the second rear sensor 268b in the illustrated case. It is also possible to move the wire brush 231 having washed the endoscope 2 until the light shielding plate 266 reaches the first rear sensor 268a. If the brush component 236 still lies within the connector tube 226 after the wire brush 231 has moved back to such a position, this brush component 236 may be washed successively and sufficiently with alkaline water, acidic water and tap water from the water supply pipe 263. After the brush component 236 is washed, the light shielding plate 266 is advanced to the second rear sensor 268b and the wire brush 31 is ready for washing the next coming endoscope 2.

While the pipe section 56 of the first washing device 51 is illustrated to have the same length as the pipe section 256 of the second washing device 52, it is possible without departing from the scope of this invention to replace these pipe sections 56, 256 by ones to be different in length. It is also possible to use the washing tank 3 in combination with only one of the first and second washing devices 51, 52.

In the washing apparatus for endoscope according to this invention, specified positions of the wire brush inserted into the pipe section are detected by the sensors to control the length of the wire brush advanced so that the length of the wire brush advanced is accurately controlled with a high reproducibility. Exchange of the wire brush can be achieved merely by insertion and withdrawal of the wire brush into and from the rear end portion of the pipe section. The wire brush is linearly received in the pipe section instead of taken up on a reel as the prior art has been the case. This feature advantageously facilitates the washing of the wire component.

What is claimed is:

1. A washing apparatus for an endoscope comprising a wire brush equipped with a wire component having front and rear end portions and a brush component provided along said front end portion, a region for housing said wire brush therein and a drive means adapted to advance/retract said wire brush from said housing toward a conduit of said endoscope and vice versa wherein:

said region including a pipe section adapted to receive a substantially full length of said wire brush inserted into and withdrawn from said region;

said region having a front end portion thereof being opened so as to be connected to said conduit;

said region having a rear end portion thereof adapted to be selectively opened and closed so that said wire brush is inserted/withdrawn into and from said pipe section when said rear end portion is opened;

said drive means being provided in the vicinity of said front end portion and functioning to advance/retract said wire brush toward and from said conduit respectively;

a water supply means being provided in the vicinity of said rear end portion to supply said pipe section with water; and said pipe section being provided at front and rear end portions thereof with at least one sensor to detect a position of said wire component respectively.

2. The washing apparatus for the endoscope according to claim 1, wherein said washing apparatus for the endoscope is used in combination with a washing tank so that said region for housing the wire brush has its rear end portion lying within said washing tank and adapted to be opened and closed within said washing tank.

3. The washing apparatus for the endoscope according to claim 2, wherein said washing tank is adapted to receive at least a pair of said washing apparatus.

4. The washing apparatus for the endoscope according to claim 1, wherein said pipe section is provided along said rear end portion with three of said position sensors arranged in a longitudinal direction of said pipe section.

5. The washing apparatus for the endoscope according to claim 1, wherein said drive means can be operated or stopped with a signal coming from any of said position sensors.

6. The washing apparatus for the endoscope according to claim 1, wherein said pipe section is light transmissive.

7. The washing apparatus for the endoscope according to claim 1, wherein said position sensors are equipped with light emitters.

8. The washing apparatus for the endoscope according to claim 1, wherein said water supply means is able to supply at least one of alkaline water, acidic water and tap water.

9. A washing apparatus for an endoscope said apparatus comprising a wire brush equipped with a wire component having front and rear end portions and a brush component provided along said front end portion, a region for housing said wire brush therein and drive means for advancing/retracting said wire brush from said housing toward a conduit of said endoscope and vice versa wherein:

said region including a pipe section adapted to receive a substantially full length of said wire brush inserted into and withdrawn from said region;

said region having a front end portion thereof being opened so as to be connected to said conduit;

said region having a rear end portion thereof adapted to be selectively opened and closed so that said wire brush is inserted/withdrawn into and from said pipe section when said rear end portion is opened;

wherein said rear end portion of said region is connected to an inside of a washing tank, said washing tank having a drain hole.

10. The washing apparatus according to claim 9, further comprising a water supply pipe connected to said pipe section to supply said pipe section with water.

11. The washing apparatus according to claim 9, wherein said front end portion of said region is formed to be connectable to said conduit of said endoscope which is to be received in said washing tank.

12. The washing apparatus according to claim 9, wherein said rear end portion of said region is adapted to be selectively opened and closed to said inside of said washing tank.

13. A washing apparatus for an endoscope, said apparatus comprising a washing tank, a wire brush equipped with a wire component having front and rear end portions and a brush component provided along said front end portion, a region for housing said wire brush therein and drive means for advancing/retracting said wire brush from said housing toward a conduit of said endoscope received in said washing tank, and vice versa wherein:

said region including a pipe section adapted to receive a substantially full length of said wire brush inserted into and withdrawn from said region;

said region having a front end portion thereof being opened so as to be connected to said conduit;

said region having a rear end portion thereof adapted to be selectively opened and closed so that said wire brush is inserted/withdrawn into and from said pipe section when said rear end portion is opened;

wherein said front and rear end portions of said region lie in said washing tank, said pipe section being provided between said front and rear end portions of said region and being extended so as to surround said washing tank.

14. The washing apparatus according to claim 13, wherein said pipe section is provided on said front end portion of said region with said drive means.

15. An apparatus for washing an endoscope, said apparatus comprising a wire brush:

a housing for accommodating said wire brush, said wire brush being moveable into and out of said housing:

a sensor for detecting a position of said wire brush relative to said housing; and a washing tank, said housing has a rear end portion lying within said washing tank and adapted to be opened and closed within said washing tank.

16. The apparatus of claim 15, wherein said housing is a pipe having both ends open to an interior of said washing tank.

17. The apparatus of claim 16, wherein said pipe has a middle section between said ends, said middle section extending circumferentially of said washing tank and located outside said washing tank.

18. The apparatus of claim 15, wherein said sensor is mounted to said housing.

19. The apparatus of claim 15, further comprising a driving element for stopping or driving said wire brush into or out of said housing in accordance with a signal coming from said sensor.

* * * * *